United States Patent
Oshida et al.

(10) Patent No.: US 6,322,364 B1
(45) Date of Patent: Nov. 27, 2001

(54) SUPERPLASTICALLY-FORMED PROSTHETIC COMPONENTS, AND EQUIPMENT FOR SAME

(75) Inventors: Yoshiki Oshida, Indianapolis; Martin Thomas Barco, II, Martinsville, both of IN (US)

(73) Assignee: Advanced Research and Technology Institute, Bloomington, IN (US)

( * ) Notice: Subject to any disclaimer, the term of this patent is extended or adjusted under 35 U.S.C. 154(b) by 0 days.

(21) Appl. No.: 09/541,924

(22) Filed: Apr. 3, 2000

Related U.S. Application Data

(62) Division of application No. 09/189,895, filed on Nov. 11, 1998, now Pat. No. 6,116,070.

(51) Int. Cl.[7] .................................................. A61C 8/00
(52) U.S. Cl. ................................................................ 433/173
(58) Field of Search .................................... 433/173, 172, 433/168.1, 200.1, 171, 201.1

(56) References Cited

U.S. PATENT DOCUMENTS

| | | |
|---|---|---|
| 788,490 | 4/1905 | Nelson . |
| 3,514,858 * | 6/1970 | Silverman ............................ 433/174 |
| 3,600,752 | 8/1971 | Kopp . |
| 3,974,673 | 8/1976 | Fosness et al. . |
| 4,113,522 | 9/1978 | Hamilton et al. . |
| 4,331,284 | 5/1982 | Schulz et al. ........................ 228/157 |
| 4,645,453 | 2/1987 | Niznick ................................ 433/173 |
| 4,767,328 | 8/1988 | Branemark ....................... 433/168.1 |
| 4,824,373 | 4/1989 | Okada et al. ..................... 433/200.1 |
| 5,004,420 | 4/1991 | Soderberg ............................ 433/172 |
| 5,030,237 | 7/1991 | Sorbie et al. .......................... 623/20 |
| 5,123,844 | 6/1992 | Wakai et al. ....................... 433/201.1 |
| 5,125,971 | 6/1992 | Nonami et al. ......................... 106/35 |
| 5,322,206 | 6/1994 | Harada et al. .................... 228/173.1 |
| 5,330,529 | 7/1994 | Cepela ..................................... 623/4 |
| 5,462,563 | 10/1995 | Shearer et al. ........................ 623/18 |
| 5,467,626 | 11/1995 | Sanders .................................. 72/60 |
| 5,516,375 | 5/1996 | Ogawa et al. ....................... 148/564 |
| 5,630,717 | 5/1997 | Zuest et al. .......................... 433/172 |
| 5,725,376 * | 3/1998 | Poirier ................................. 433/172 |

OTHER PUBLICATIONS

3M Bateman UPFII Universal Proximal Fmur Brochure, 21 pages, ORT–092–H (159515) UN.

(List continued on next page.)

*Primary Examiner*—John J. Wilson
*Assistant Examiner*—Melba Bumgarner
(74) *Attorney, Agent, or Firm*—Woodard, Emhardt, Naughton, Moriarty & McNett

(57) ABSTRACT

Described are unique prosthesis systems including superplastically-formed prosthetic elements, and methods and an apparatus for forming such elements. A preferred dental prosthesis system includes at least two osseointegrated fixtures, abutments attached to the fixtures, a bar member interconnecting the abutments, and a prosthesis detachably connected to the bar member, wherein the prosthesis includes a superplastically-formed metal element having a surface conforming to the bar member and abutments, a resin denture base attached to the metal element, and artificial teeth mounted on the resin denture base. The preferred prosthetic components are prepared by superplastic forming under temperature conditions which are repeatedly cycled above and below the transformation temperature of the metal being formed. In this fashion, metal components having excellent microstructures are prepared, which exhibit characteristic high strength, superior corrosion resistance and excellent dimensional accuracy and stability as well.

12 Claims, 8 Drawing Sheets

OTHER PUBLICATIONS

BråneMark System® Overdenture Options poster, USB 316 8.96 ©Nobel Biocare USA, Inc. (1996).

*Journal of the JSTP*, vol. 27, No. 302, pp. 357–364 (1986–3).

Curtis, R.V.; Juszczyk, A.S.: Walter, J.D.: Swale, B., "Ti–6Al–4V Dental Implant Superstructures", *Titanium '95*, Proceedings of the Eight World Conference of Titanium Held at the International Convention Centre, Birmingham, UK, pp. 1784–1791, Oct. 22–26, 1995.

Curtis, R.V.; Juszczyk, A.S. and Walter, J.D., Poster CZ0326.

Curtis, R.V.; Juszczyk, A.S. and Walter, J.D., "Abstract No. 123", Divisional Abstracts: The British Society for Dental Research, *J. Dent. Res.*, vol. 74, No. 3 (1995).

Mudford, L.; Curtis, R.V., Walter, J.D., "An Investigation of Debonding Between Heat–Cured PMMA and Titanium Alloy (Ti–6Al–4V)", *J. Dentistry*, vol. 25, No. 5, pp. 415–421 (1997).

Oshida, Y., "An Application of Superplasticity to Powder Metallurgy", *J. of the Japan Soc. Of Powder and Powder Metallurgy*, vol. 22, No. 147, pp. 1–7 (1975).

Oshida, Y., "Transformation Plasticity of Steel and Titanium Alloys in Compression", Abstract of Thesis, Waseda University, Tokyo, Japan (1965).

Sadowsy, S.J. (D.D.S.), "The Implant–Supported Prosthesis for the Endentulous Arch: Design Considerations", *J. Prosthetic Dentistry*, vol. 78, No. 1, pp. 28–33 (Jul. 1997).

Takase, S.; Oshida, Y. "Application of Dynamic Superlasticity to Solid–State Bonding of Cast Irons to Different Ferrous Alloys", pp. 349–354.

Takase, S.; Oshida, Y., "On the Solid–State Bonding in Cast Irons Using Dynamic Superplastic Phenomena", *Transactions ISU*, vol. 17, pp. 506–515 (1977).

Takase, S.; Oshida, Y., "On the Solid–State Bonding of Same Material in Cast Irons", pp. 273–279.

Wakabayashi, N. (DDS, PhD., M. Ai, DDS PhD), "A Short–Term Clinical Follow–Up Study of Superplastic Titanium Allow for Major Connectors of Removable Partial Dentures", *j. of Prosthetic Dentistry*, vol. 77, No. 6, pp. 583–585.

Wakabayashi, N. (DDS, PhD., M. Ai, DDS PhD), "Thisckness and Accuracy of Superplastic Ti–6Al–4V Alloy Denture Frameworks", *Internat'l J. Prosthedontics*, vol. 9, Np. 6, pp. 520–526 (Nov. 6, 1996).

* cited by examiner

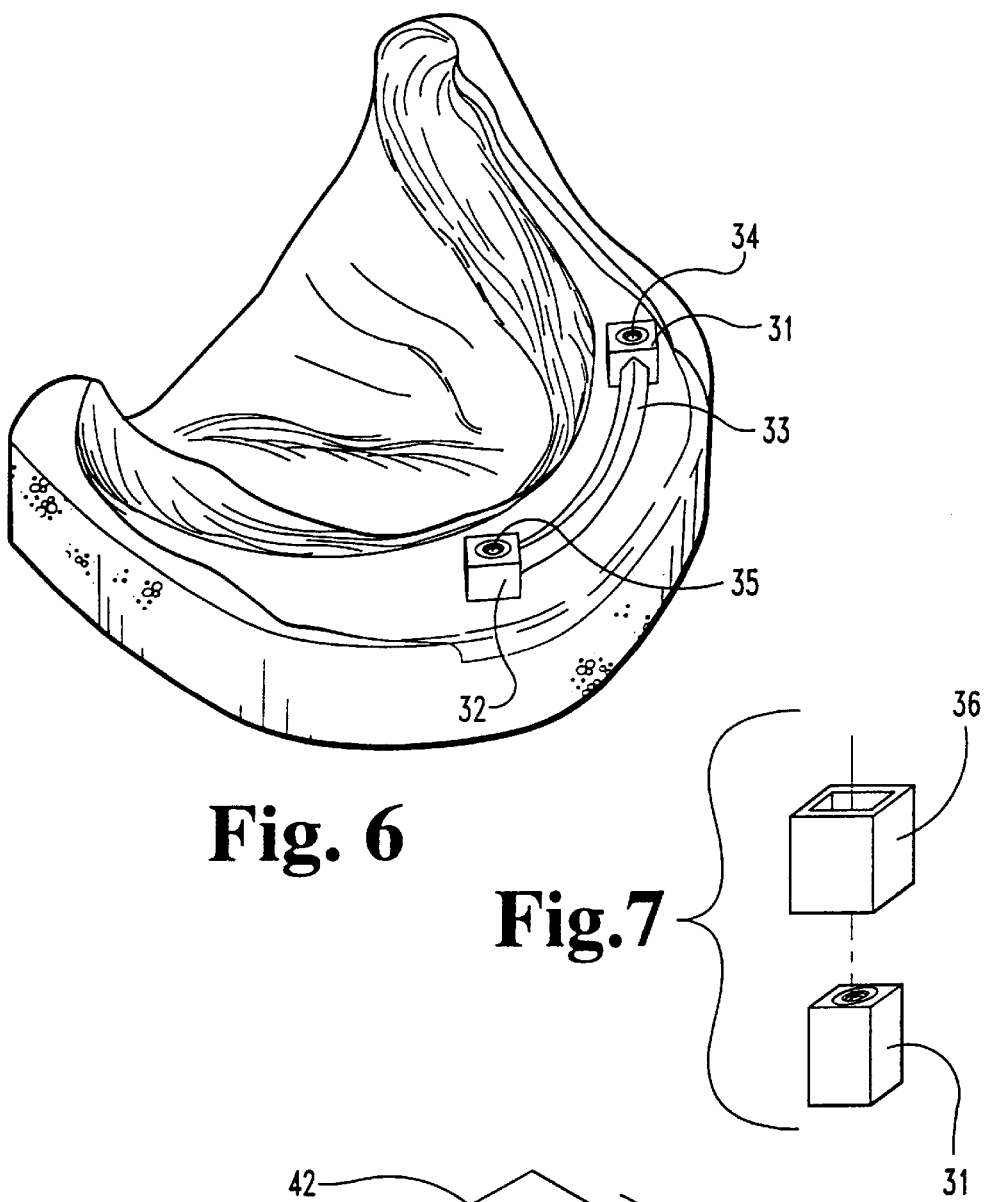
Fig. 6
Fig. 7
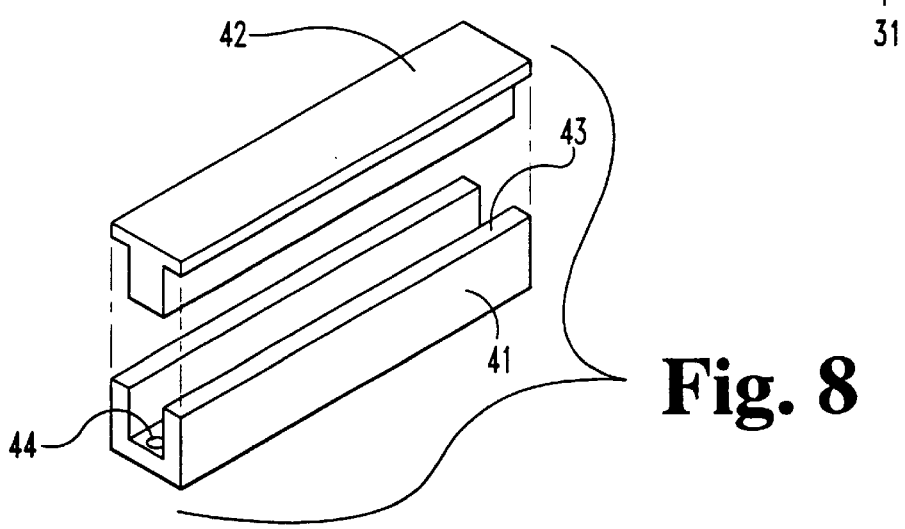
Fig. 8

SUPERPLASTICALLY-FORMED PROSTHETIC COMPONENTS, AND EQUIPMENT FOR SAME

This application is a divisional of application Ser. No. 09/189,895 filed Nov. 11, 1998, now U.S. Pat. No. 6,116, 070.

BACKGROUND

The present invention relates generally to prosthetics. More particularly, the invention relates to novel prosthetic systems incorporating unique superplastically-formed components, and to methods and equipment useful for fabricating the same.

The use of implanted prostheses in patient care is widespread. For example, dental endosteal implants are currently considered the standard of care for patients with missing teeth. As an illustration, a patient who is totally endentulous or is missing a large number of teeth may elect to have three to ten implants placed in either the maxilla or mandible, which become fixed or "osseointegrated" in the bone structure. These implants are often used to anchor a superstructure, which ultimately supports and distributes forces transmitted through an attached denture.

For purposes of illustration, a conventional method for preparing a superstructural prosthesis can be summarized as follows. First, an assembled implant will include a fixture, an abutment, and an abutment screw attaching the abutment to the fixture. Several such implants are placed into a cavity prepared in the jawbone structure, for example the mandible.

After the placed implants are osseointegrated (usually from 4 to 6 months after implantation), a corresponding number of gold or titanium cylinders are placed over the abutments. After careful work on investing and wax-up, a gold bar element is cast, which includes screw access holes to attach to the abutments. A denture prosthesis is fabricated including a removable denture base (usually fabricated from acrylic resin) to which an appropriate number of artificial teeth are processed and mounted. The denture prosthesis is ultimately connected to the implant-supported bar in an attachable/detachable manner.

There are several ways to attach the denture prosthesis ultimately to the implants. For instance, several artificial teeth mounted on the denture prosthesis may have central holes through which retaining screws are inserted, to extend through the underlying abutments and gold cylinders and thread into inner threaded portions of the connecting screws. Alternatively, a posterior side portion of the partial denture base can be provided with an extended base in which holes are made. Retaining screws are then placed through the holes into the inner threads of the connecting screws. In a further retention method, retaining clips may be attached to the undersurface (inner side) of the partial denture base. These clips are frictionally-engaged in a detachable manner to bar portions of the gold bar element.

The practical application of osseointegrated dental implant systems presents several challenges. Because natural teeth are fixed in the jaw bone through a periodontal membrane, an occlusal abnormality within biological limits will not cause any damage to the tooth structure. On the other hand, with an osseointegrated implant, the fixture lacks a periodontal membrane and anything less than a passive fit of a suprastructure to the implants may have an adverse influence directly on the jawbone structure. Moreover, such an abnormality will also cause a premature deterioration on the superstructure. Accordingly, the ideal superstructure will be prepared to provide a precise fit, taking into account mechanical environmental factors including stress load distribution and impact load condition.

As to dental implants systems overall, in general, it is believed that their long-term success is governed not only by good osseointegration of the endoseous implants to bone, but also by: (1) suitable biomechanics, materials and surface morphology; (2) correct indication and favorable anatomic conditions (bone and mucosa); (3) good operative technique; (4) patient cooperation (oral hygiene); and (5) adequate material selection and design/fabrication of the superstructure.

Osseointegrated dental implant systems can have overdentures that are either fixed or detachable. Detachable overdentures provide more versatility than fixed-overdentures. For instance, overdentures can be placed when there is an insufficient number of fixtures and/or when the fixtures are in a poor position for contouring a fixed prosthesis. In addition, still other anatomic, physiologic, esthetic, or oral hygiene limitations might dictate against an indication of a fixed prosthesis, requiring the use of a detachable overdenture.

As indicated above, a first component of an overall dental endosteal implant system is the implants themselves. Several important selection parameters for implant materials include tissue compatibility, corrosion resistance, fatigue strength, specific gravity, friction coefficient, and corrosive effect on other materials with higher potential. Given these parameters, titanium and several types of titanium-based alloys are preferred materials for implant fabrication.

Among the many different types of implants which have been developed, specifically, for promoting osseointegration, the Nobelbiocare implant system (which has merged with Sterioss implants), the IMZ (Intramobile Zylinder) implant system, (Implant, Innovation Incorp.) and the ITI (Internationale Team für Implantologie) implant system are widely used. In the Nobelbiocare system, a fixture component made of unalloyed titanium is implanted into the bone structure. A component passing through the mucous membrane, known as an abutment, is connected to the fixture by abutment screws. Both the abutment and the abutment screws are also fabricated from unalloyed titanium. The upper surface of the abutment is connected to a gold cylinder, which forms a portion of the superstructure The IMZ implant system is designed specifically for use with a patient's remaining natural dentition. Its three major components include an implant main body (unalloyed titanium substrate plasma spray-coated with titanium beads or hydroxyapatite powders), a transmucosal implant extension component which is implanted into the bone through the mucosa membrane, and an intramobile element or an intramobile connector. The intramobile element is normally manufactured using polyoxymethylene (POM) resins, having an excellent viscoelastic characteristics and mechanical properties. The intramobile connector is made of unalloyed titanium and is constructed in the form of a unified component of intramobile element and screw, the unified structure being connected to the POM disk. A plastic shock absorber, internally threaded to accept a prosthesis retention screw, screws into the implant to reduce stress on the bone surrounding the implant.

The ITI implant is characterized by a hollow cylinder structure. This implant is usually fabricated from unalloyed titanium, which is cold-worked to stabilize the crystalline structure and enhance its modulus of elasticity and toughness.

As indicated above, the overall system includes a separately-fabricated superstructure anchored to the implant(s). Various retention mechanisms have been employed for this anchorage, and the particular mechanism selected is important to the success of the system. Primary objectives of a superstructure retention mechanism are to make the superstructure detachable to make post-implantation observation/examination easier, to make the prosthesis adjustable (if necessary), and to provide for convenient extraction of the implants should a problem develop.

Retention bars are most commonly used for the retention mechanism, and are generally preferred because they provide strong retention force—typically providing at least 400 g of retention force to resist the attachment/detachment movement. Conventionally, retention bars are made of cast gold alloy (Type VI, containing 8~17 weight % of Ag, 9~16 weight % of Cu, up to 10 weight % of Pd, 0.2~8 weight % of Pt, and up to 3 weight % of Zn), although they are also sometimes cast from a silver-palladium alloy. The retention bar is firmly attached to the head portions of pre-placed implants. One mechanism for retaining the partial denture to the bar uses a plurality of bar riders, or clips, mounted on the bar. A corresponding number of clip retainers (or riders) are then placed on the undersurface of prosthesis base to cooperate with the bar riders.

Other retention methods include, for example, retention studs. These rely on a relatively small occlusal retention force, and thus provide less mechanical retention force than bar attachments. A resilient snap attachment is used with the IMZ implant, and includes a patrix which is screw-inserted into the implant main body and a cooperating matrix mounted inside the denture base. Other systems may use a Zagg or Zest attachment where limited space is a problem.

Similar to the selection of the material for implants, the selection of materials for the superstructure is very important. Several requirements for an optimal superstructure material include (1) excellent biocompatibility; (2) good electrochemical corrosion resistance; (3) light specific gravity; (4) compatibility to the elastic modulus of the receiving bone; (5) good physical strength and endurance; (6) excellent formability and dimensional stability; (7) less contamination of bacteria; and (8) good galvanic corrosion resistance. Three basic material groups have received serious consideration for use in superstructures, including metals, ceramics and polymeric resins/composites. Metals have been most promising because they best meet the aforementioned requirements. A variety of metals are available for fabricating a single crown to bone-anchored bridge. These include type IV hard gold alloy, gold-silver-palladium alloy, and commercially pure titanium and its alloys. However, Ni and Co elements are electrochemically unstable in-vivo. Co, Ni, Cu, Ag and V elements are considered toxic. Particularly, Ni element shows hypersensitivity and oncogenecity. Accordingly, gold alloys and titanium materials are preferred. It is generally believed that gold alloys exhibit excellent physical properties, castability, solderability, marginal fit, and relaxing the occlusal pressure.

Before any abrasive cleaning or finishing of the casting is done, the gold cylinders should be protected with protection caps or altered replicas. Negligence in this area may cause damage to the interface surfaces. This is one of the most critical steps in the prosthesis fabrication. Failure to protect the interface surfaces at this point will result in destroying the seats of the prosthesis.

There are several complications that occur in dental implant systems. Complications associated with the fixture (implant) are the most severe and usually result in loss of the fixture, including lack of or loss of osseointegration, fixture fracture, or mandibular fracture. If a terminal abutment is lost, any cantilevered extension on that side needs to be shortened if a fixed prosthesis is to be maintained. This shortening of the occlusal extension may result in loss of stability of an opposing complete denture. A less serious and infrequent complication associated with the fixture is that of dehiscence of the implant.

Loosening or breakage of the abutment screw hexagonal head can also occur. A screw that is fractured within the fixture is more difficult to remove because of limited visibility and access. Soft tissue inflammation and hyperplasia around the abutment can also occur. This finding is usually associated with a poor fit of the bar to the abutments which place stresses and strains on the integrated implant, which eventually lead to implant failure.

A loose abutment cylinder not only mechanically irritates the mucosa, but also allows an excessive accumulation of microorganisms at the interface between the abutment and implant fixtures. Ideally, the abutment cylinders must project 2–3 mm above the mucosal margin. If the interface between the gold cylinder and the abutment is not precise, then premature dehiscence will occur.

If the bar splint (which is used to accommodate attachments) is extensive, it may limit the potential for making a totally mucosa-born prosthesis, and distribution of loading forces between the mucosa and the splint is a factor in prosthesis assembly.

Complications associated with the denture prosthesis itself are the least threatening to the survival of the tissue-integrated prosthesis. These complications (breakage or dislodgement of acrylic resin teeth) are usually related to staining, wear, or breakage. The most common prosthesis problem is loosening or breakage of gold locking screws, with resultant loosening of the prosthesis.

There are some complications which can be significant, and more importantly, which indicate flaws associated with the design or fabrication of the implant-supported prosthesis. On occasion an overdenture or a fixed bone-anchored bridge framework will fracture. The most common fracture site is the area just distal to the terminal implant fixture (extension). Most such fractures are caused either by inadequate bulk in this region, or by voids or discrepancies formed during casting.

Prosthetic elements for implantation in other areas of the body also suffer several related disadvantages. Such elements desirably include components of maximal strength, minimal weight, and good resistance to electrochemical corrosion. Moreover, in many instances the prosthesis must include surfaces which conform and effectively cooperate with surfaces of other implanted structures, with anatomical features of the patient, or both.

In light of this background, there remain needs for novel prosthetic components that are lightweight, dimensionally accurate, and strong, and which exhibit superior corrosion resistance. Desirably, such components will be fabricated using accepted biomaterials and methods that are readily adapted to clinical practice. The present invention addresses these needs.

SUMMARY OF THE INVENTION

Accordingly, preferred embodiments of the invention provide a method for fabricating a first prosthetic component for implantation in a patient, and a component prepared by the method. In accordance with the invention this method comprises providing a die having a surface corresponding to an anatomical feature of the patient, a surface of a second prosthetic component, or both. A sheet of a superplastically-formable metal is subjected to superplastic forming on the die, wherein the forming is conducted using a temperature profile repeatedly cycled above and below the transformation temperature of the metal during at least a portion of the overall forming process. In this manner, a prosthetic component of extraordinarily high strength and accuracy can be obtained. Still further, prosthetic components so prepared will exhibit superior electrochemical corrosion resistance due to retention or development of an ultrafine microstructure during preparation. In accordance with this aspect of the invention, the prosthetic component fabricated may be of a dental, hip, knee, elbow, shoulder, ankle, finger, eye or nasal prosthesis, for example. In some forms, the second prosthetic component may be adapted for fixed attachment to a bone of the patient. Also, the die surface is often convex, and/or the first and second components may be a socket and ball-type combination respectively, as occurs in many joint prosthetic systems.

Still another preferred embodiment of the present invention provides a dental prosthesis system. This system includes at least two osseointegratable fixtures, and abutments for attachment to the fixtures. An elongate attachment member interconnects the abutments. A prosthesis is detachably connectable to the attachment member, wherein the prosthesis includes a metal element having a surface conforming to the attachment member and which has been obtained using superplastic forming preferably with a temperature profile repeatedly cycled above and below the transformation temperature of the metal. A resin prosthesis is attached to the superplastically-formed element, and artificial teeth are mounted on the resin prosthesis.

A still further preferred embodiment of the present invention provides an apparatus for superplastic forming of a dental prosthesis. The inventive apparatus includes an upper pressure vessel, and a lower pressure vessel for fluid-tight connection to the upper pressure vessel. A high pressure gas inlet tube and a high pressure gas release valve are provided to the upper pressure vessel, and a heat source is positioned within the upper pressure vessel. A device, for instance a thermocouple, is provided for monitoring the temperature of the metal sheet. The apparatus also includes means for receiving the metal sheet between the lower pressure vessel and the upper pressure vessel, and a cooling block within the lower pressure vessel and adapted to support a mold block on which the metal sheet is to be formed. At least one cooling fluid passageway occurs within the cooling block for circulating a cooling fluid, and at least one cooling fluid inlet tube and at least one cooling fluid outlet tube are fluidly connected to the cooling fluid passageway. The more preferred apparatus also includes control means for controlling the temperature in the upper pressure vessel, which is operable to repeatedly cycle the temperature to first and second pre-selected temperatures.

The present invention addresses several drawbacks associated with prosthetic components fabricated by other means. For example, the invention provides light-weight, strong and dimensionally-accurate prosthesis components having an ultrafine grain structure, which avoid the occurrence of defects associated with conventional casting techniques, including for instance voids, shrinkage, and cavities. Further, the invention provides prosthetic components of extreme dimensional and configurational accuracy and dimensional stability, enabling optimization of their cooperation with other prosthetic components in the system and/or with anatomic features of the patient. In addition, the invention provides prosthetic components exhibiting superior electrochemical corrosion resistance. These and other objects and advantages of the invention will be apparent upon reviewing the descriptions herein.

DESCRIPTION OF THE DRAWINGS

FIG. 6 provides a perspective view of a dental stone cast according to the present invention, with a connecting bar component, and a pair of column-shaped abutments connected to placed implants.

FIG. 7 provides a perspective view of a column-shaped abutment, and a corresponding box-shaped housing to be attached at its upper surface to undersurface of a fabricated denture prosthesis of the invention.

FIG. 8 shows further another preferred embodiment, according to the invention, showing a connecting couple comprising a connecting bar with a recess and a mating component having an undersurface with a corresponding projection for friction fit within the recess.

DESCRIPTION OF THE PREFERRED EMBODIMENTS

Figure 1:
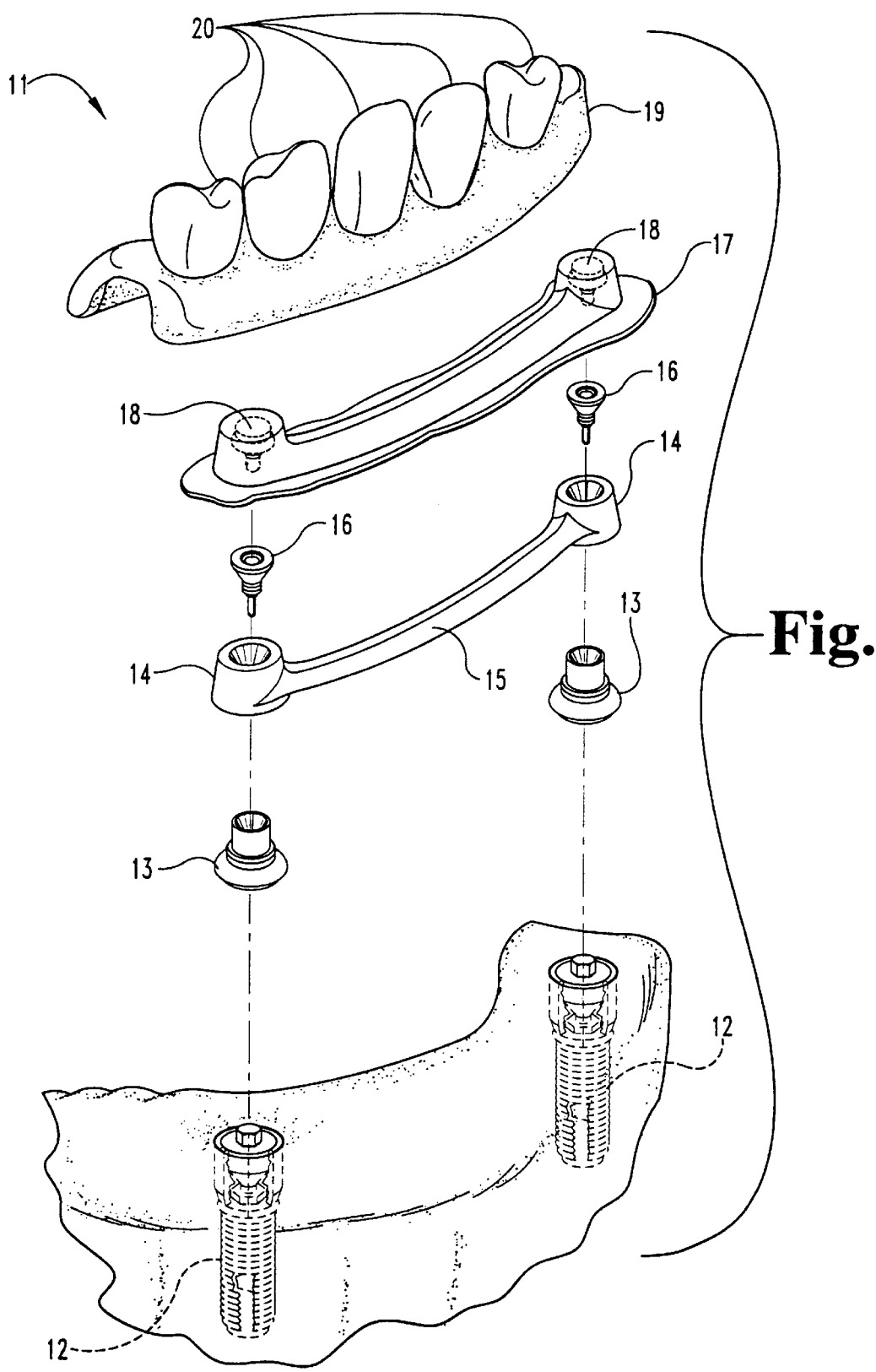
FIG. 1 provides an exploded, perspective view of a preferred dental prosthesis system of the present invention FIG. 2 provides a perspective view of a dental stone cast according to the present invention, with a connecting bar component and a pair of conical abutments connected to placed implants.

For the purpose of promoting an understanding of the principles of the invention, reference will now be made to certain embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention relates.

As disclosed above, one aspect of the present invention provides novel prosthetic components which have been fabricated by superplastic forming (SPF) using a specified temperature profile, and methods and apparatuses useful for their fabrication. As is known, superplasticity is a solid-state deformation phenomenon characterized by both neck-free elongation and vanishing flow stress, observed in a processing temperature range [Y. Oshida, "Transformation Plasticity of Steels and Titanium Alloys in Compression" Master's Thesis, Syracuse University, Syracuse N.Y., 1967]. In addition to providing a large and uniform deformation, SPF generates very little residual stress during and after the SPF process. Thus, excellent dimensional stability can be achieved, and the formed article will generally present low if any risk of mechanical-assisted deterioration such as an in-vivo stress corrosion cracking. Superplastic forming also offers precision (or near net-shape) forming at a solid state condition, generally at a temperature at or below one half of the absolute melting point of the material concerned. Further, superplastically formed products of the invention do not contain any external or internal defects/voids typically associated with cast structures, and are essentially free from residual stresses.

In one aspect of the invention, preferred prosthetic components are prepared using a specified temperature profile, in which the temperature of the metal sheet being formed is cycled repeatedly above and below the phase transformation temperature of the metal, during at least a portion of the forming period. With this technique, "transformation plasticity" is used during forming, which is generally rationalized in terms of deformation during structural rearrangements associated with a phase transformation between low temperature phase and high temperature phase [Y. Oshida, Master's Thesis, Syracuse University, Syracuse N.Y., 1967].

Such transformation superplastic forming techniques as described above differ from those which depend upon so-called "micrograin plasticity". During micrograin superplastic formation, the material is subjected to a constant operational temperature while applying a relatively small working force. During such processing, ultra fine-grained materials (1 to 10 microns) exhibit superplastic flow within a narrow elevated temperature range at low strain rates (in a range from about $10^{-5}$ to $10^{-3}$ sec$^{-1}$). Optimal materials for use in this type of SPF must be heat-treated to develop a very fine microstructure prior to the SPF operation, and the mechanisms proposed for micrograin plasticity include diffusional processes (e.g., volume, grain boundary diffusion etc.) and grain boundary sliding. In addition, the pre-heat-treated microstructure with ultra-fine grain sizes is normally worsened during and after the microgram SPF operation, resulting in lower mechanical strength and poor corrosion resistance.

SPF techniques utilizing transformation plasticity has several significant advantages over those using only microgram SPF. Materials formed with transformation SPF have a characteristic, high strength, and an ultrafine microstructure that is generally not coarsened relative to that of the starting material. Further, the working material does not need to be previously heat-treated to refine its grain size, because transformation SPF provides the ability to refine the grain structure of the metal due to the thermo-mechanical heat treatment involved in the process. Thus, SPF utilizing transformation superplasticity generally provides prosthetic components for use in humans and other animals that are superior to those produced by micrograin SPF.

As to materials suitable for use in the invention, it is generally understood that if the strain rate sensitivity exponent "m" of a material is larger than 0.3, the material can be considered superplastic. When the "m" value reaches 1.0, the material exhibits visco-elastic flow. The "m" values of titanium and its alloys are reported to range from 0.7 to close to 1.0, indicating that these materials are highly suitable for superplastic forming.

Titanium and titanium alloys are thus preferred metals for use in the superplastic forming operation. These include for instance commercially pure titanium (CPT) and titanium alloyed with one or metals from selected from the group consisting of aluminum, vanadium, niobium, molybdenum, iron and zirconium. Illustrative titanium alloys include Ti-6Al-4V, Ti-5Al-2.5Fe, Ti-20Cr-0.2Si, Ti-25Pd-5Cr, Ti-6Al-7Nb, and Ti-4.5Al-3V-2Fe-2Mo. In the identification of titanium alloys herein, standard nomenclature is used in which the elements alloyed with the titanium are preceded by their weight percent in the overall alloy.

In one aspect of the invention, SPF using transformation plasticity is used to form a superstructural denture base element. A polymeric resin member on which artificial teeth are mounted can be attached to this superstructural denture base element to form a complete prosthesis configured to fit securely and with extreme accuracy over a bar interconnecting osseointegrated implants in the patient. In addition, the superplastically-formed denture base element can optionally include a portion or portions extending beyond the profile of the underlying bar/implant structure, to cover endentulous mucosa adjacent the bar/implant structure, e.g. more posterior edentulous mucosa of the patient. This technique is highly clinician friendly, in that it avoids other more time consuming and costly fabrication techniques presently used, and provides a prosthetic component of high strength and accuracy.

In another aspect of the invention, if the prosthesis component has an intricate shape, or one or more auxiliary elements needs to be bonded to the net piece for insertion, superplastic forming and diffusion bonding (SPF/DB) (again in the solid-state) can be employed to bond two or more members which together form the prostheses, and/or to bond the prosthesis to the auxiliary element(s).

The use of titanium and its alloys in the present invention provides a higher specific strength (higher ratio of mechanical strength divided by specific gravity) than that provided by other metals. For example, type IV gold alloy (composed of about 8–17% by weight Ag, about 9–15% by weight Cu, about 0–10% by weight Pd, about 0.2–8% by weight Pt, and about 0–2% by weight Zn) has 490 MPa of ultimate tensile strength, 400 MPa of yield strength, and 88 GPa of modulus of elasticity, and a specific gravity of 18.3 g/cm$^3$. Accordingly, the specific strength of the gold alloy is about 27 ($\approx$490/18.3). On the other hand, commercially pure titanium has 490 MPa of ultimate strength, 450 MPa of yield strength and 100 GPa of modulus of elasticity, and a typical Ti-based alloy, Ti-6Al-4V, has 980 MPa ultimate strength, 920 MPa yield strength, and 120 GPa modulus of elasticity. It is reported that titanium has a specific gravity of 4.51 g/cm$^3$. Thus, the specific strength of CPT is approximately 109 ($\approx$490/4.51) and the specific strength of Ti-6Al-4 alloy is about 217 ($\approx$980/4.51).

Pure titanium has an allotropic phase transformation temperature of 883° C., at which a low temperature alpha-phase (hexagonal close-packed crystalline structure) changes to a high temperature beta-phase (body-centered cubic crystalline structure) on heating, and this transformation is reversible on a cooling, too. There are basically three types of titanium alloys available: (1) alpha-type; (2) beta-type; and (3) alpha plus beta type. The alpha phase possesses a better weldability and creep resistance, and is lighter than the beta phase. On the other hand, the beta phase (or beta alloy) exhibits better heat-treatability, and plastic formability than the alpha alloy. Alpha plus beta alloy has somewhat a mixed properties of both alpha and beta alloys. In order to stabilize the alpha alloys Al, Sn, Zr, O, and N are usually added to the alloy. To stabilize beta alloys, V, Mo, Fe, Cr, Mn, and Cu elements are typically added to the alloy. When the alloy is to be used as a prosthesis for vital tissue, e.g. as a biomedical material, biological compatibility and high corrosion resistance are important.

Currently, the following titanium materials are considered preferred for use as biomaterials: commercially pure titanium, and Ti-5~6Al-X alpha-beta alloys, where X elements may include 4V, 7Nb, 2Mo-2Fe, 2.5Fe, and 3Mo-4Zr.

As indicated above, during transformation superplastic forming, the temperature of the material is cycled to first and second temperatures above and below, respectively, its phase transformation temperature. As illustrations, CPT can be so formed while cycling between temperatures of about 720° and about 920° C., and Ti-6Al-4V can be so formed while cycling between temperatures of about 790° and about 1,000° C. The room temperature flow stress of CPT is about 500 MPa, and the typical transformation superplastic forming stress is in a range from about 1 to about 3 MPa. The room temperature flow stress of Ti-6Al-4V is approximately 1,000 MPa; while its typical transformation superplastic forming stress, and that of other titanium alloys, is usually about 3 to about 5 MPa. It will be understood that these temperature and stress values are preferred and illustrative, and that those of ordinary skill in the field will be readily able to select and use suitable temperature and stress parameters in the present invention given the teachings herein.

Referring now specifically to FIG. 1, illustrated is a preferred dental prosthesis system 11 of the invention. Prosthesis system 11 includes placed implants 12 (each including a fixture, abutment and an abutment screw), and cylinders 13 (e.g. fabricated from a gold alloy) corresponding to the implants 12. System 11 also includes a bar element having abutments 14 interconnected by an elongate bar portion 15. Bar element can be fabricated, for instance, by casting. Illustratively, the bar element may cast of gold or a gold alloy. Retaining screws (not shown) extend down through abutments 14 and cylinders 13 and are threaded into the internally-threaded heads of the abutment screws of the implants 12. Matrices 16 are bonded into abutments 14. A superplastically-formed partial denture base 17 is provided, and patrices 18 are bonded to its undersurface at locations corresponding to the matrices 16. Patrices 18 (shown in phantom) cooperate with matrices 16 to provide a friction-based attachment-detachment system for the denture base 17. Denture base 17, in turn, is bonded to an acrylic resin denture 19 having a plurality of artificial teeth 20 mounted thereon.

As indicated, denture base element 17 of FIG. 1 is prepared using superplastic forming. The preferred forming process includes transformation superplastic forming alone or in combination with an earlier micrograin superplastic forming process. In this regard, it is advantageous in accordance with the invention to utilize a transformation superplastic forming process as a final forming technique, to provide an improved, refined grain structure to the formed element.

Figure 2:
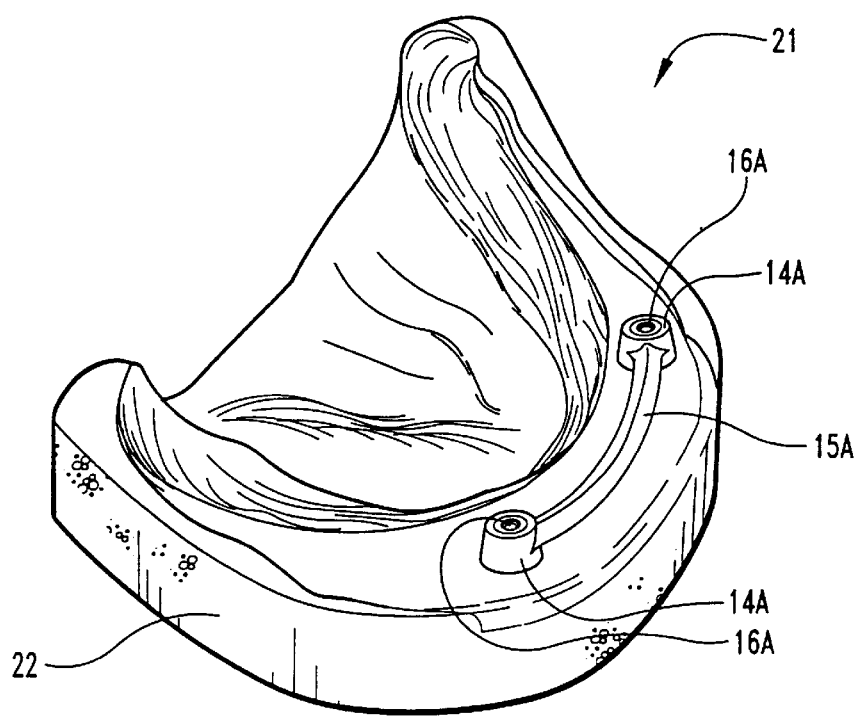

Referring now to FIG. 2, shown is an article 21 which can be employed as a die in a superplastic forming process to prepare the denture base element 17. Article 21 includes a dental stone cast 22. Replicates of underlying components of the overall system are mounted on the cast 22, including implant replicates (not shown), cylinder replicates (not shown), a bar element replicate including abutments 14A, a connecting bar portion 15A, retaining screw replicates (not shown), and matrice replicates (16A). It will be understood that the presence of all such elements is preferred, but will not be absolutely required in all instances, with the important feature being that the die present a three-dimensional configuration replicating that which will exist in the patient.

Figure 3:
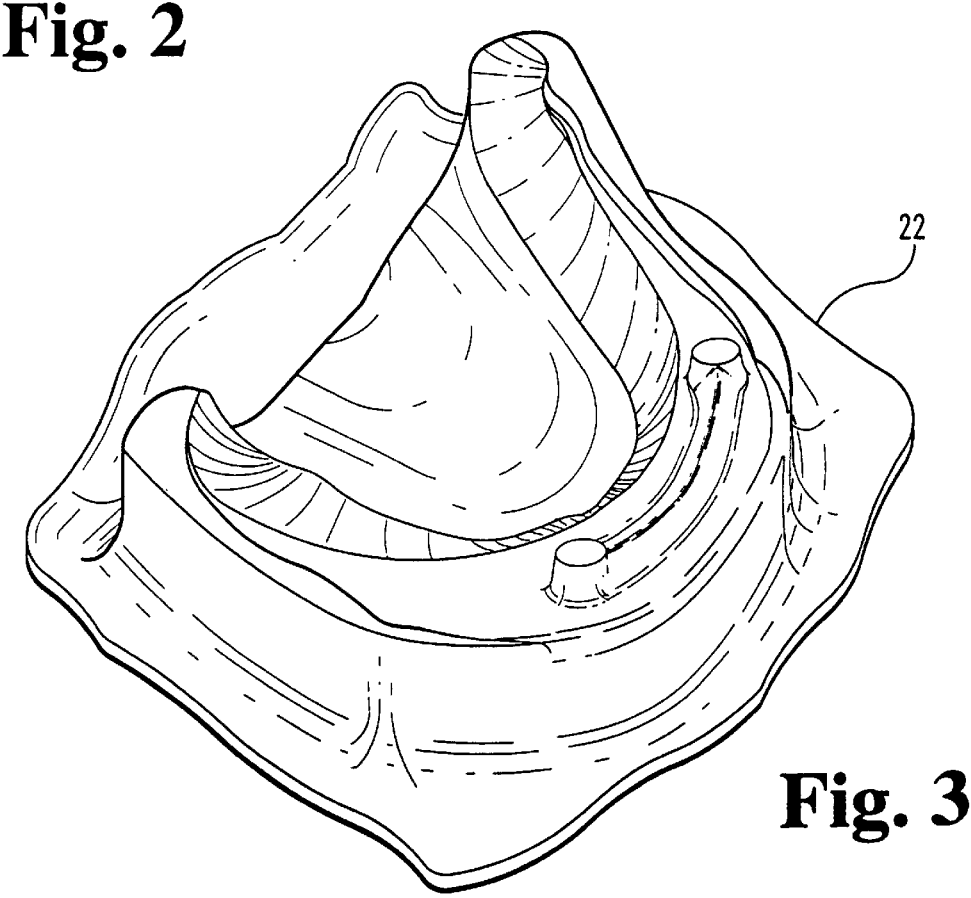
FIG. 3 provides a perspective view of the dental stone cast of FIG. 2, having superplastically formed thereover a thin metal sheet.

The completed article 21 is then used as a die in a superplastic forming process. Accordingly, a thin sheet 22 of a superplastically-formable metal is superplastically formed over article 21 using a temperature profile repeatedly cycled above and below the transformation temperature of the metal, providing a structure as illustrated in FIG. 3. The desired base element 17 is then cut out of the formed sheet 22, using for example standard dental cutting equipment.

The superplastic forming used in the present invention is preferably performed in an inventive apparatus having the following components, functions, and characteristics. The apparatus comprises an upper pressure vessel having a central high pressure gas inlet tube and lower pressure vessel having a circular shoulder portion on its vessel for securing the thin metal sheet. The assembled upper and lower vessel chambers should be constructed as a fluid-tight structure of sufficient mechanical integrity to withstand the forces to be developed during the forming process. Structures withstanding a compressive force of about 50 Mpa should be suitable for most applications. The die to which the thin metal sheet will be formed (e.g. article 21, FIG. 2) is placed in the working space in side the lower vessel chamber. Heating can be achieved by coil heaters mounted inside the upper and lower vessel chambers. An inert gas such as nitrogen or argon, preferably argon, is introduced through the central pressure gas inlet tube to form the thin metal sheet. In an alternative or additional manner, the compressive load can be applied using a solid, male die member positioned within the upper chamber. Still further, such compressive loads applied to the metal sheet surface opposite the female die can be replaced by or supplemented by creating a relatively lower pressure environment, e.g. a vacuum, in the bottom portion of the lower chamber.

The metal sheet to be superplastically formed is preferably heated at a moderate rate that is not to fast for control, yet not so slow as to make the process impracticable. If the rate is too fast, the occurring temperature for phase transformation is shifted to a higher temperature on heating and a lower temperature on cooling than those reported. On the other hand, if it is too slow, it will not be practical. Advantageous heating rates are about 10° to about 20° C./min. Similarly, the forming force can be applied prior to or after reaching the forming temperature. It is preferred, however, to begin application of the forming force when the chamber temperature reaches close to half of the desired forming temperature. In this regard, in the case of transformation superplastic forming, the forming temperature can be defined as an intermediate temperature between the maximum and minimum temperatures. The forming force is typically kept constant during the forming and until the chamber temperature decreases again to below abut half of the forming temperature in the cooling stage of the process.

In the case of transformation superplastic forming, the minimum and maximum temperatures will be controlled sufficiently to achieve the transformation process, while avoiding the occurrence of adverse microstructural changes such as grain growth that might occur if the maximum temperature is too high. In this regard, during the forming process, the maximum temperature will desirably be about 30° to about 50° C. above the transformation temperature of the material to be formed, and the minimum temperature will be about 30° to about 50° C. below the transformation temperature.

Dental stone casts to be used in forming processes of the invention can be made of conventional materials, provided that they are selected to withstand the conditions of forming, including the forming force and forming temperature. In this regard, a reinforced material can be used, for example a $CaO—ZrO_2—TiO_2$ mixture. In addition, a lubricant such as BN powder can be applied between the cast surface and the work sheet metal, to facilitate removal of the formed sheet upon completion of the forming process.

Figure 9:
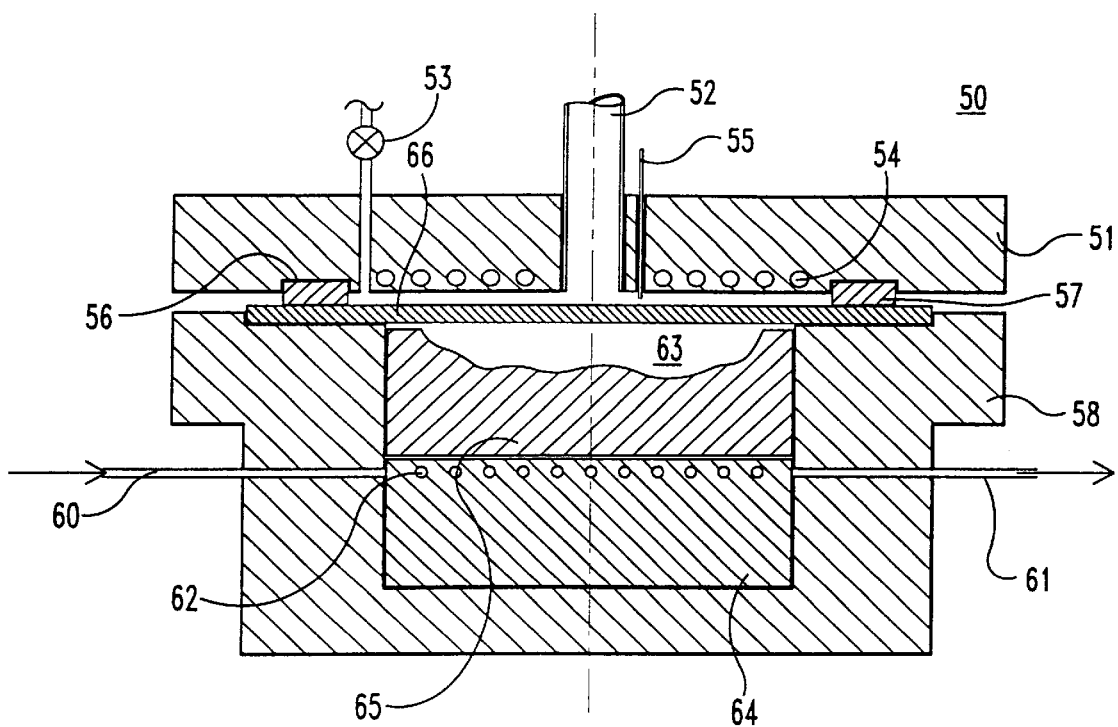
FIG. 9 shows cross-sectional view of a superplastic forming apparatus of the present invention.
Figure 10:
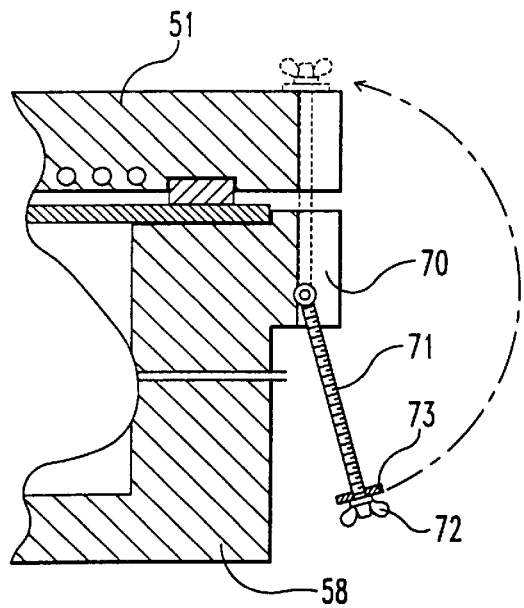
FIG. 10 shows a locking mechanism for the apparatus shown in FIG. 9.

Referring to FIGS. 9 and 10, illustrated is a preferred apparatus of the invention which can be used for superplastic forming. The apparatus includes a main body 50 including an upper pressure vessel 51 and a lower pressure vessel 58. The upper and lower pressure vessels 51 and 58 are manufactured separately and assembled together by, for example, a hinge-type engaging means (FIG. 10). Upper pressure vessel 51 has a centrally-located high pressure gas inlet tube 52. The proximal end of gas inlet tube 52 is connected to a gas cylinder containing an inert gas such as argon or nitrogen (not shown). A high pressure vessel gas release valve 53 is also provided and is connected to a safety valve.

A thermocouple 55 is extends into in internal chamber of upper pressure vessel 51, and is fixed and sealed firmly adjacent to the high pressure gas inlet tube 52. The distal end of the thermocouple 55 is positioned in an area immediately adjacent to the location in which a sheet material is to be superplastically formed, and serves to monitor the material temperature during a forming operation.

A circular groove 56 is formed on a bottom face of the upper vessel 51 and is configured to hold a circular metallic seal ring 57. A plurality of electrical heating coils 54 are also mounted on the bottom face of upper vessel, in a position effective to heat the internal chamber formed by upper vessel 51. The coils 54 are in turn connected to an AC power supply (not shown).

A circular shoulder 59 is provided on an upper face of a lower pressure vessel 58, and serves to receive sheet material 66 to be superplastically formed. A cooling water inlet tube 60 and a cooling water outlet tube 61 extend through a wall thickness of the lower pressure vessel 58, and are held firmly thereon. Both upper vessel 51 and lower vessel 58 can be made, for example, of AISI type 304 stainless steel.

A chamber 63, formed by inner side walls and an inner bottom wall of the lower pressure vessel 58, contains a cooling base block 64 and a mold block 65; the latter is received on top of the cooling base block 64. Near the top face of the cooling block 64, a passageway for circulating a cooling fluid is provided, e.g. by plurality of cooling water tubes 62. The ends of the cooling tubes 62 are connected to the cooling water inlet tube 60 and the cooling water outlet tube 61, respectively.

Describing now a basic forming procedure which can be conducted with the above apparatus, first, a precise mold is made by replicating a patient denture or other anatomical pattern, as illustrated with a top wavy pattern of mold block 65. The mold material can be a standard casting mold (e.g. a phosphate bonded investment material), reinforced with zirconia or alumina (by about 5–10% by volume) to retard the reactivity and to enhance the compressive strength of the casting mold. After hardening of the mold block 65, the block 65 is set upon the cooling base block 64 within the chamber 63. The cooling block 64 is securely fixed to inner sides of the lower pressure vessel 58 and coupled with the cooling inlet/outlet tubes 60 and 61.

Next, a metal sheet 66 is set upon the circular shoulder portion 59 formed on top face of the lower pressure vessel 58. After engaging a metallic seal ring 57 (e.g. made of AISI type 304 stainless steel) to the circular groove 56, the upper and lower pressure vessels 51 and 58 are tightly fixed by, for example, a plurality of hinge mechanisms as shown in FIG. 10 located about the apparatus. For instance, a plurality of hinge mechanisms can be provided having distal ends pivotally engaged at a corner portion 70 of lower pressure vessel 58. The hinge mechanisms each include a hinge screw bar 71 having a proximal end provided with a top nut 72 and a washer ring 73. Alternatively, top nut 72 and washer ring 73 may be manufactured as a single piece. To connect the upper and lower pressure vessel, bar 71 swings up and is received into a groove in the outer surfaces of corner portion 70 and upper vessel 51. The top nut 72 is then tightened to urge the washer ring 73 against the upper surface of upper vessel 51, thus forcing upper vessel 51 and lower vessel 58 firmly together.

At this stage of the process, the metal sheet 66, which is sandwiched firmly between the upper and lower pressure vessels 51 and 58 by the metallic seal ring 57, is ready to be superplastically formed and optionally superplastically diffusion bonded to attachments including, for example, crowns or bridges. The sheet metal material can be, for example, commercially pure titanium (CPT), Ti-6Al-4V, Ti-5Al-2.5Fe, Ti-6Al-7Nb, Ti4.5Al-3V-2Fe-2Mo, Ti-20Cr-0.2Si, or Ti-25Pd-5Cr. The thickness of sheets made of titanium and its alloys is preferably between 0.1 and 1.0 mm, and depends upon the mechanical strength of the selected material at room temperature as well as its effective superplastic forming temperature ranges.

To achieve transformation superplastic forming and/or diffusion bonding, the $\beta$-transus of the selected material should be used. In this regard, the $\beta$-transus is a phase transformation between $\alpha$-phase in the $\alpha+\beta$ dualphase region of Ti-based alloys or a single $\alpha$ phase in CPT, and $\beta$ phase which is stable at higher temperature. In order to obtain an effective transformation superplasticity of the material, the material is heated and cooled such that on both heating and cooling the material exhibits this phase transformation. Thus, the material should be subjected to the $\alpha$ (hexagonal closed packed structure)→$\beta$ (body centered cubic structure) phase transformation on each heating process and the $\beta$→$\alpha$ phase transformation on each cooling process of the thermal cycle pattern. Illustratively, the $\beta$-transus of CPT is about 880° C. and that of the most Ti-based alloys is approximately 950° C. The thermal cycle should be selected such that the maximum temperature is the $\beta$-transus temperature plus about 30 to about 50° C., and the minimum temperature is the $\beta$-transus minus about 30 to about 50° C.

While applying such a cycled temperature pattern to the sheet metal, a working load is be applied to cause plastic deformation, resulting in a transformation superplasticity. There are several ways to apply such flow stress onto the work piece, including for instance mechanical pressing or hydraulic pressing. According to the present invention, hydraulic pressing is preferably employed. Therefore, unlike conventional mechanical pressing, both male and female molds are not required—only a female mold or die needs to be prepared by replicating a patient's denture pattern or other anatomical feature.

Figure 12:
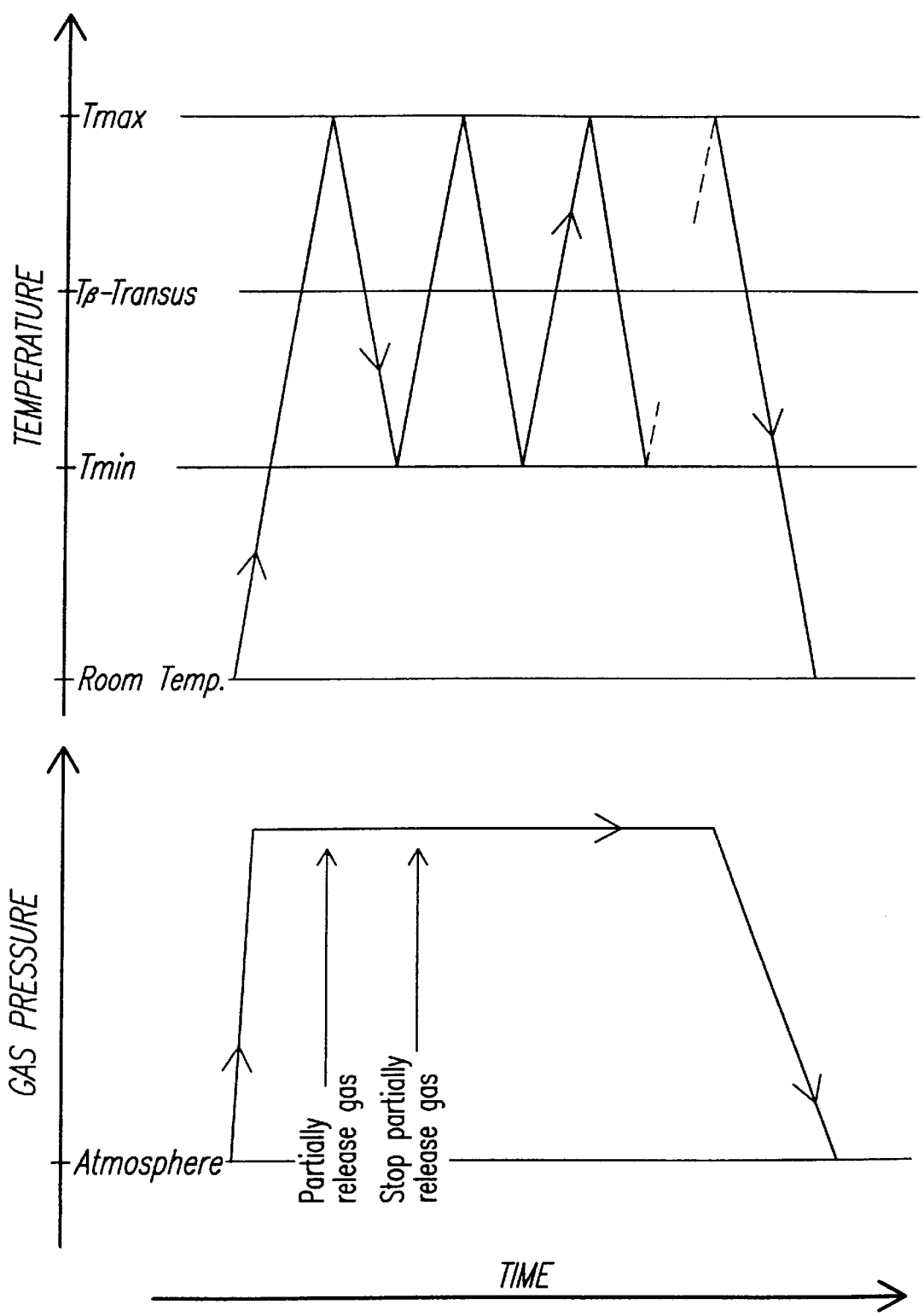
FIG. 12 provides schematic diagrams showing temperature and pressure profiles as a function of time for a metal sheet during transformation and micrograin superplastic forming.

FIG. 12 provides schematic diagrams for temperature and pressure of the sheet metal as a function of time, from the point of setting the sheet metal in the forming apparatus to the final stage of the forming. The thermal cycle employed in transformation superplastic forming can be achieved in several ways. For example, the thermocouple 55 can be used to monitor the temperature of the sheet metal surface, and this signal can be used as feedback to the power supply source, which in turn regulates temperature by regulating to power supply to the heating coils 54. In another embodiment, the temperature cycling can be provided by manipulating the high pressure gas release valve 53 and the high pressure gas inlet tube 52, while maintaining a constant power supply to the heating coils 54 sufficient to provide the maximum temperature of each thermal cycle. In particular, when the thermocouple 55 signals achievement of the maximum temperature of a thermal cycle, the release valve 53 is opened. Simultaneously, a regulator (not shown) connected to gas inlet tube 52 is synchronized to the amount of the released gas and is activated to add a corresponding amount of gas (at room temperature) to increase the pressure within the forming chamber to maintain a constant forming force, also causing a decrease in the temperature of the metal sheet. This process is continued until the thermocouple 55 signals that the sheet metal temperature has decreased to the minimum temperature of the thermal cycle. The regulator and valve for the gas inlet tube 52 and the gas release valve 53 are then simultaneously closed, whereupon the sheet metal is heated again from the minimum temperature to the maximum temperature in the next thermal cycle. This process is repeated several times to complete the transformation superplastic forming of denture bases.

Transformation superplastic forming as described above provides several advantages. For instance, the room temperature flow stress of Ti-6Al-4V is approximately 1,000 MPa, while the required flow stress for micrograin superplasticity is reported to be about 20 to about 50 MPa. On the other hand, only about 1 MPa of gas pressure is needed for transformation superplastic forming as described. The strain per cycle is about 0.5%, and a complete denture base can be fabricated after only a few (for instance 10) thermal cycles, which is approximately equivalent to about 15–20 minute working time in a preferred process. In addition, the microstructure of the formed material can be refined, e.g. a Ti-6Al-4V alloy having an initial grain size of about 25 to about 30 $\mu$m can be refined to have an average grain size of about 2.5 $\mu$m.

For purposes of promoting a further understanding of the present invention, including its various aspects and advantages, the following Examples are provided. It will be understood that these Examples are illustrative, and not limiting, of the present invention.

EXAMPLE 1

With reference to FIG. 1, illustrated is a clinical situation in which the patient has existing teeth from the second premolars and all molars on both sides. Hence, a partial denture covering from first premolar from left side to the first premolar on right side is needed. Namely, a supporting device for a partial removable denture includes implants 12, cylinders 13, a bar component including abutments 14 and bar portion 15, and matrices 16 mounted in abutments 14.

To address this clinical situation, a dental stone cast is prepared as illustrated in FIG. 2 using Zircon-Sand investing material. Replicates of the above-noted implants, cylinders, bar component, and matrices are mounted in the cast. Transformation superplastic forming technology is employed using a commercially pure titanium sheet (0.55 mm thick). The forming is conducted in an inert argon ambient, and the argon pressure is increased to 1.75 MPa when the forming chamber temperature reaches 600° C. The forming temperature is cycled between 720° C. as a minimum temperature and 920° C. as a maximum temperature, under heating rate of 15° C./min and a cooling rate of 13° C./min. After the forming is complete (see e.g. FIG. 3), the material is cooled while maintaining the forming force until the temperature reaches 600° C. After complete cooling, the superplastically-formed denture base 17 is cut from the sheet. Patrices 17 are soldered to the undersurface of the base in locations corresponding to the matrices 16 of the underlying superstructure. An acrylic resin base 19 having artificial teeth 20 mounted thereon is prepared, and is bonded to the superplastically-formed element. The prosthesis provides an excellent fit.

EXAMPLE 2

The procedures of Example 1 are repeated except that the sheet material is Ti-6Al-4V (0.62 mm thick), the forming temperature cycle is between 790° C. as a minimum temperature and 1,000° C. as a maximum temperature, and the forming pressure is 4.2 MPa. Again the result is very satisfactory.

EXAMPLE 3

The recommended prosthesis in this case has two implants placed on first premolars, two cantilevers are prepared in a single cast structure, a full arch denture base, and artificial teeth are processed and mounted in a full arch acrylic resin denture. The prosthesis is a fixed removable prosthesis.

Figure 4:
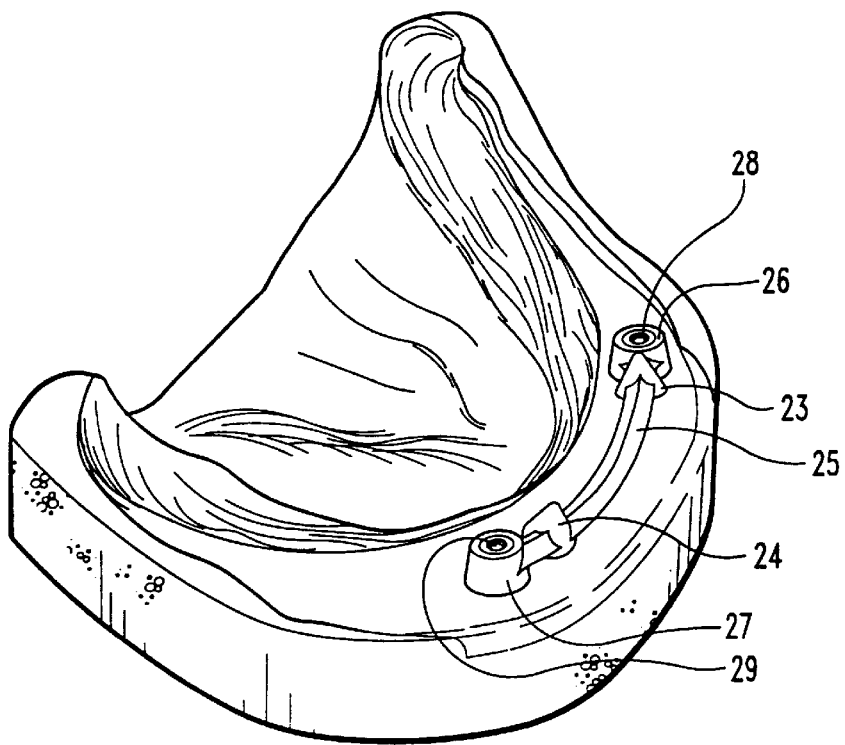
FIG. 4 provides a perspective view of a dental stone cast according to the present invention, with a connecting bar component, a pair of abutments connected to placed implants, and a pair of cantilevers with retaining matrices.

Referring to FIG. 4, shown is a perspective view of a dental stone cast of a patient having an edentulous mandible jaw. The cast is fabricated using Zircon-Sand investing material (consisting primarily of $ZrO_2$, $SiO_2$ and Zr), and comprises a bar component which includes abutments 23 and 24 interconnected by bar portion 25. Cantilevers 27 and 28 are connected to the of abutments on their proximal ends. The abutments 23 and 24, bar portion 25 and cantilevers 26 and 27 are cast (e.g. of gold or gold alloy) in a single piece. Abutments 23 and 24 are connected to threaded portions of the placed implants. Matrices 28 and 29 are positioned and cemented on the top portions of cantilevers 26 and 27.

Figure 5:
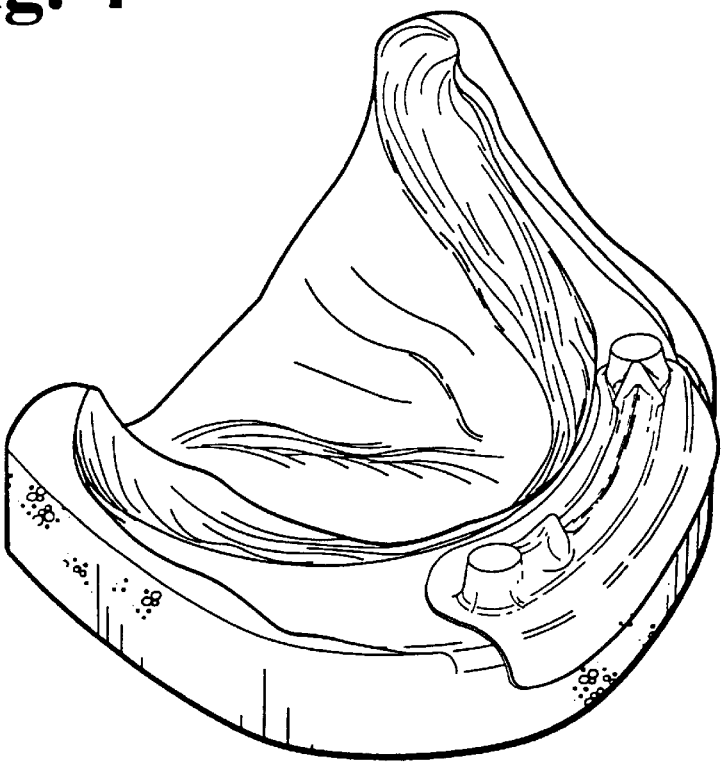
FIG. 5 provides a perspective view of the dental stone cast of FIG. 4, having superplastically formed thereover a thin metal sheet, and showing a prosthesis cut from the formed sheet.

The above stone cast is used as a die to superplastically form a commercially pure titanium metal sheet (0.55 mm thick) in an inert argon ambient under the conditions described in Example 1. The superplastically formed sheet is removed from the cast and the prosthesis is cut out (see FIG. 5).

Two patrices (not shown) are soldered to appropriate locations on superplastically formed prosthesis. An acrylic resin denture having artificial teeth mounted thereon is bonded to the superplastically formed prosthesis. The prosthesis is nicely fitted to a patient having implants, abutments, cantilevers, bar implants and matrices corresponding to those in the stone cast.

EXAMPLE 4

The procedures of Example 3 are repeated, except that a metal sheet of a titanium-aluminum-vanadium alloy (Ti- 6Al-4V, 0.62 mm sheet thickness) is employed, and the conditions for superplastic forming are as described in Example 2. The result is very satisfactory.

EXAMPLE 5

A commercially pure titanium sheet (0.55 mm thick) with relatively large grain size (>20 $\mu$m) is used to fabricate a superplastically-formed denture base 17 as illustrated in FIG. 1, using a microgram superplastic forming stage followed by a transformation superplastic forming stage. For the microgram superplastic forming, the temperature is held constant at 950° C. and the pressure of the argon gas is held at 6.5 MPa. The conditions for transformation superplastic forming are as described in Example 1. After 10 temperature cycles are completed, the material is allowed to cool and the superplastically-formed base element is cut from the sheet. An acrylic resin base having artificial teeth mounted thereon is bonded to the formed element. The prosthesis provides an excellent fit.

EXAMPLE 6

The procedures of Example 5 are repeated, except that the micrograin superplastic forming stage is preceded by a transformation superplastic forming cycle similar to the latter cycle. This is necessary because the sheet initially has a coarse microstructure. Again, the prosthesis provides an excellent fit and dimensional accuracy.

EXAMPLE 7

A superstructural prosthesis as illustrated in FIG. 6 is prepared. In particular, the prosthesis includes a pair of retaining abutments 31 and 32 having a generally rectangular cross-section (e.g. made of Ti-6Al-4V) interconnected by a bar portion 33 (e.g. made of a titanium material or a type IV gold alloy). The bar portion 33 is cast-in-cast with the retaining abutments 31 and 32 to fabricate this structure. As illustrated, holes 34 and 35 are provided to affix this device to the threaded head portions of abutment screws of the implants. The dental stone cast is made with Zircon-Sand investment material.

Superplastic forming and diffusion bonding are simultaneously employed in this Example. The sheet metal is commercially pure titanium (0.55 mm thick with 5 $\mu$m grain size). A pair of rectangular box-shaped housings 36 and 37 (see FIG. 7, in which housing 37 is not shown but is identical to 36) are fabricated from Ti-6Al-4V alloy and sized to fit snugly over retaining abutments 31 and 32, respectively. Housings 36 and 37 are positioned at locations on the stone cast corresponding to retaining abutments 31 and 32. The diffusion coefficient during transformation superplasticity is much faster than that during microgram superplasticity. Accordingly, transformation superplasticity was selected as the preferred method to fabricate the prosthesis and diffusion-bond the housings 35 and 36 to the formed element. In addition, the temperature cycle pattern and forming force utilized in the Examples above for transformation superplasticity of Ti-6Al-4V alloy were used. After completion of the forming cycle, it is found that the housings 36 and 37 are nicely diffusion bonded to the formed sheet. The prosthesis is cut from the formed sheet, and a resin denture base with mounted artificial teeth is attached as in the Examples above. The resulting prosthesis provides an excellent fit, and the contacting wall areas between the housings 36 and 37 and retaining abutments 31 and 32 provide frictional force to detachably retain the prosthesis in place over the underlying superstructure.

EXAMPLE 8

With reference to FIG. 8, the prosthesis of this Example employs a bar 41 having a central recess or channel interconnecting a plurality of implants. The bottom portion of the channel has two screw holes 43 and 44 through which tightening screws are passed into an inner threaded portion of the abutment screws of the implants. A dental stone cast is prepared having implants and the bar 41 thus connected to the implants. This cast is used as a die for superplastic forming and simultaneous diffusion bonding similar to that carried out in Example 7, except that a mating component 42 having a projection corresponding to the central channel of bar 41 is positioned and diffusion bonded to the formed metal sheet instead of the housings 35 and 36 of Example 7. After forming, the prosthesis element including the diffusion bonded mating component 42 is cut from the sheet. A resin denture base with mounted teeth is attached to this element, which provides an excellently-fit prosthesis for a patient having corresponding implants retaining a corresponding bar 41.

EXAMPLE 9

Figure 11:
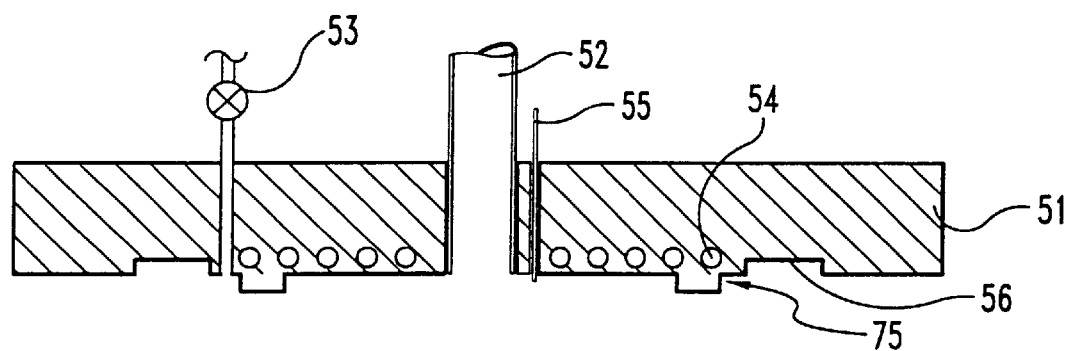
FIG. 11 provides a cross-sectional view of an alternate upper pressure vessel for the apparatus of FIG. 9.

This example describes another use of simultaneous superplastic forming and diffusion bonding according to the present invention. Referring to FIG. 11, shown is a cross-sectional view of only an upper pressure vessel of a superplastic forming apparatus. The remaining components are identical to those described in connection with FIG. 9 above. All numbered parts in FIG. 11 are identical to those seen in FIG. 9 except for bonding shoulder portion 75 in FIG. 11. In accordance with this Example, crown(s) or bridge(s) are placed and sandwiched between the bonding shoulder portion 75 and the upper face of the sheet metal 66. If the sheet metal and attachments (e.g. crowns or bridges) are made of the same material (e.g. both are made from CPT), the exactly same thermal cycle pattern and gas pressure flow stress can be supplied to perform SPF/DB. If the sheet metal material is dissimilar material to that of the crowns or bridges, the thermal cycle pattern on both heating and cooling stages should include both materials' $\beta$-transus temperatures. Accordingly, in the case of a CPT denture base ($\beta$-transus of about 880° C.) and a Ti-6Al-4V crown ($\beta$-transus of about 950° C.), the minimum temperature in FIG. 14 should be 880° C. less about 30–50° C. and the maximum temperature should be 950° C. plus about 30–50° C. Using such an SPF/DB process and approximately 15 thermal cycles, a peeling bond strength of the crown to the denture base is about 840–880 MPa, which is about 85–90 percent of the tensile strength of the crown material (Ti-6Al-4V).

EXAMPLE 10

In this Example, the SPF/DB process of Example 9 is repeated, except that titanium powder is inserted between the sheet metal and the crown stem prior to the SPF/DB processing.

EXAMPLE 11

Figure 13:
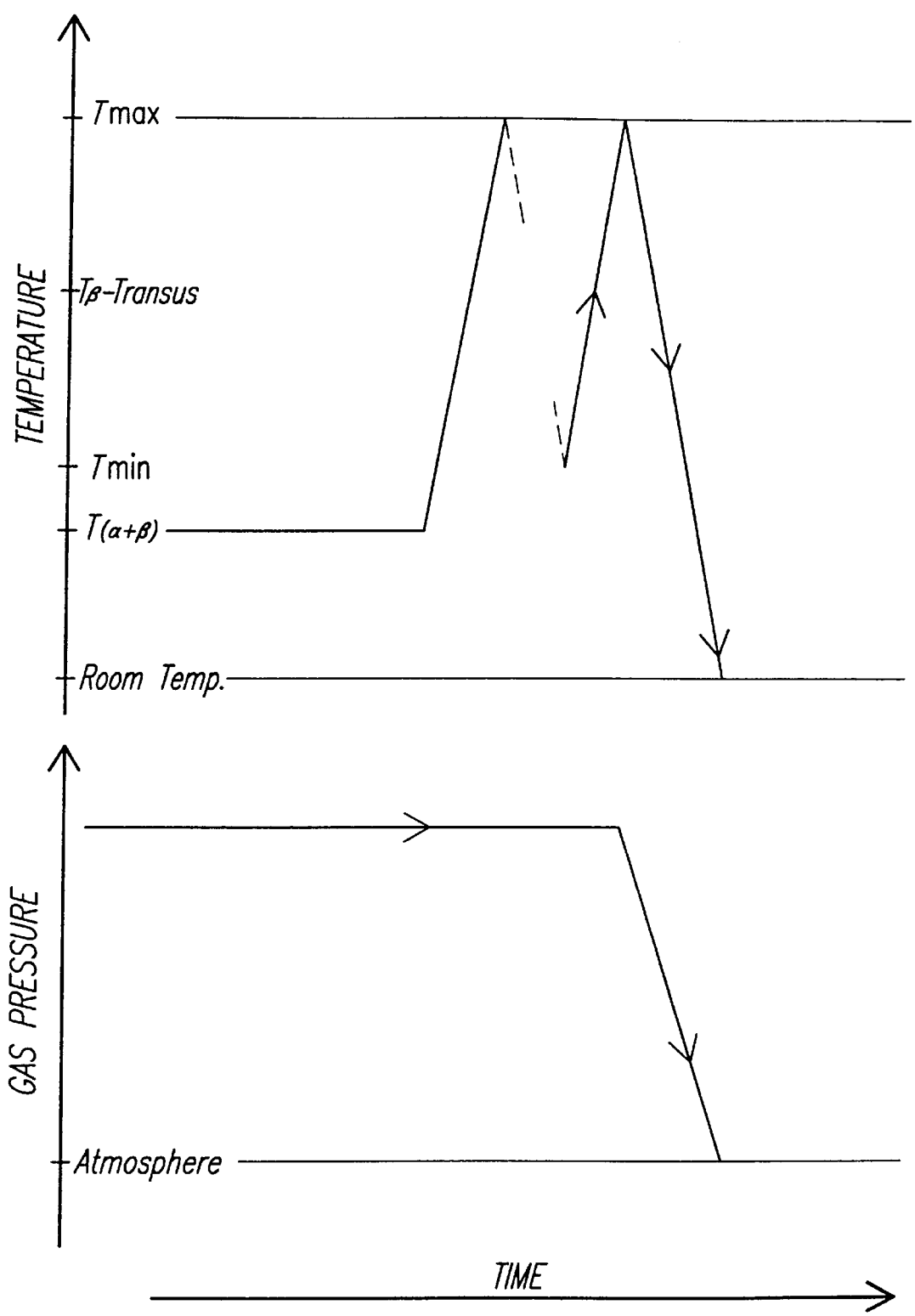
FIG. 13 provides a schematic diagram showing temperature and pressure profiles as a function of time for a metal sheet during a superplastic forming cycle that achieves both transformation superplasticity and micrograin superplasticity.

As described previously, an originally course microstructure can be refined remarkably using transformation superplastic forming. The refined microstructure is achieved by a so-called thermo-mechanical heat-treatment. Thus, in this Example, an apparatus as illustrated in FIGS. 9 and 10 is used to form a Ti-6Al-4V metal sheet in the preparation of a denture base 17 as in FIG. 1. In this process, the metal sheet is subjected to microgram superplastic forming at a constant temperature of about 850° C. followed by transformation superplastic forming (e.g. for about 5 thermal cycles), as illustrated in FIG. 13. In this manner, the microstructures are refined by the latter forming process.

While this invention has been explained in detail in the foregoing description, it will be understood that the invention is not limited to the specific embodiments disclosed. Rather, many modifications and variations will be apparent to those of skill in the art and may be practiced without departing form the spirit and scope of the present invention. For example, in accordance with the invention, superplastic forming may be employed to fabricate components for use in other prosthesis systems in which near net-shape forming provides an advantageous cooperation among two components of the system and/or between a system component and an anatomical feature of the patient. For example, superplastic forming can be employed to fabricate components of other orthopedic implant systems including for example, hip, knee, elbow, shoulder, ankle, finger, eye and nasal prostheses. Moreover, dies for use in such superplastic forming process can be prepared using conventional three-dimensional imaging/modeling technology, avoiding the need for casts of patient anatomy and/or cooperating prosthesis components.

What is claimed is:

1. A dental prosthesis system, comprising:
   at least two osseointegrated fixtures;
   abutments attached to said fixtures;
   a bar member interconnecting said abutments; and
   a prosthesis detachably connected to said bar member, said prosthesis including
   (i) a metal base element having a surface conforming to said bar member and abutments, said metal base element formed by superplastic forming with a temperature profile repeatedly cycled above and below the transformation temperature of a metallic material of the metal base element, (ii) a resin denture base attached to said metal base element, and (iii) artificial teeth mounted on said resin denture base.

2. The dental prosthesis system of claim 1, wherein said metallic material is titanium or an alloy of titanium.

3. The dental prosthesis system of claim 2, wherein said metallic material is a titanium alloy.

4. The dental prosthesis system of claim 3, wherein said metallic material is titanium alloyed with one or more members selected from the group consisting of aluminum, vanadium, niobium, molybdenum, iron and zirconium.

5. The dental prosthesis system of claim 4, wherein the metallic material is selected from the group consisting of Ti-6Al-4V, Ti-6Al-7Nb, Ti-5Al-2Mo-2Fe, Ti-5Al-2.5Fe and Ti-5Al-3Mo-4Zr.

6. The dental prosthesis system of claim 1, wherein said superplastic forming is conducted with a temperature repeatedly cycled between a first temperature below the transformation temperature of said metallic material and a second temperature above the transformation temperature of said metallic material, wherein said first temperature is at least about 30° C. below said transformation temperature, and said second temperature is at least about 30° C. above said transformation temperature.

7. The dental prosthesis system of claim 6, wherein said metallic material is titanium or a titanium alloy.

8. The dental prosthesis system of claim 7, wherein said metallic material is a titanium alloy.

9. The dental prosthesis system of claim 8, wherein said metallic material is titanium alloyed with one or more members selected from the group consisting of aluminum, vanadium, niobium, molybdenum, iron and zirconium.

10. The dental prosthesis system of claim 9, wherein said metallic material is selected from the group consisting of Ti-6Al-4V, Ti-6Al-7Nb, Ti-5Al-2Mo-2Fe, Ti-5Al-2.5Fe and Ti-5Al-3Mo-4Zr.

11. The dental prosthesis system of claim 6, wherein said metal is commercially pure titanium.

12. The dental prosthesis system of claim 6, wherein said superplastic forming includes applying a forming force of about 1 to about 3 MPa.

* * * * *